United States Patent [19]

Fields et al.

[11] Patent Number: 5,563,032
[45] Date of Patent: Oct. 8, 1996

[54] MOSAIC POLYPEPTIDE AND METHODS FOR DETECTING THE HEPATITIS E VIRUS

[75] Inventors: Howard A. Fields, Marietta; Yury E. Khudyakov; Michael O. Favorov, both of Atlanta, all of Ga.

[73] Assignee: The United States of America as represented by the Department of Health and Human Services, Washington, D.C.

[21] Appl. No.: 196,945

[22] Filed: Feb. 15, 1994

Related U.S. Application Data

[63] Continuation-in-part of Ser. No. 965,667, Oct. 21, 1992.

[51] Int. Cl.$^6$ ............................ C12Q 1/70; C07K 14/08
[52] U.S. Cl. ............................ 435/5; 530/350; 435/69.3; 436/820; 436/518
[58] Field of Search .................... 530/350; 435/5, 435/69.3; 436/518, 820

[56] References Cited

PUBLICATIONS

Khudyakov et al. *Virol.* 198:390–393, 1994.
Khudyakov et al. *J. Gen. Virol.* 75:641–646, 1994.
Favorov et al. *J. Virol. Meth* 46:237–250, 1994.
Khudyakov et al. *Virol.* 194:89–96, 1993.
Chien et al. *Proc. Natl. Acad. Sci. USA* 89:10011–10015, Nov. 1992.
Dawson et al. *J. Virol. Meth* 38:175–186, 1992.
Kumar et al. *Gene* 110:137–144, 1992.
Goldsmith et al. *The Lancet* 339:328–331, 1992.
Tam et al. *Virology* 185(1):120–131, Nov. 1991.
Yarborough et al. *J. Virol.* 65(11):5790–5796, Aug. 1991.
Ichikawa et al. *Microbiol. Immunol.* 35(7):535–543, Apr. 1991.
Reyes et al. *Gastroenteriologia Japonica* 26(3):142–147, 1991.
Reyes et al. *Elsevier Sci. Pub. B.V.* (*Biomed. Div.*) Chapter 43:237–245, 1991.
Reyes et al. *Science* 247:1335–1339, Mar. 1990.
Bradley et al. *Proc. Natl. Acad. Sci. USA* 84:6277–2681, May 1987.
Alkhatib et al., "The Predicted Primary Structure of the Measles Virus Hemagglutinin," *Virology* 150:479–490 (1986) Spec. p. 12, lines 14–19.
Drillion et al., "Protection of mice from fatal measles encephalitis by vaccination with vacinnia virus recombinants encoding either the hemagglutinin or the fusion protein," *Proc. Nat'l Acad. Sci. USA* 85: 1252–58 (1988).
Hilleman et al., "Development and Evaluation of the Moraten Measles Virus Vaccine," *JAMA* 206: 587–90 (1968) Spec. p. 1, lines 14–19.
Richardson et al., "The Nucleotide Sequence of the mRNA Encoding the Fusion Protein of Measles Virus (Edmonton Strain): A comparison of Fusion Proteins from Several Different Paramyxoviruses," *Virology* 155: 508–523 (1986) Spec. p. 12, lines 15–19.

*Primary Examiner*—Mary E. Mosher
*Assistant Examiner*—Donna C. Wortman
*Attorney, Agent, or Firm*—Needle & Rosenberg, P.C.

[57] ABSTRACT

A nucleic acid encoding a mosaic hepatitis E virus (HEV) polypeptide, consisting of the nucleotide sequence defined in the Sequence Listing as SEQ ID NO:1 is provided. A nucleic acid encoding epitopes 5, 6, 22, 23, 28 and 29 of hepatitis E virus and substantially lacking the nucleic acids intervening the epitope-coding nucleic acids in the native hepatitis E virus is also provided. An isolated nucleic acid that selectively hybridizes under stringent conditions with the mosaic polypeptide-encoding nucleic acid and has at least 70% sequence identity with SEQ ID NO:1 is provided. Also provided are such nucleic acids having at least 80%, 90% and 95% sequence identity. A polypeptide consisting essentially of the amino acid sequence defined in the Sequence Listing as SEQ ID NO:2 is provided. Polypeptides encoded by the present selectively hybridizing nucleic acids, and nucleic acids encoding epitopes 5, 6, 22, 23, 28 and 29 of HEV and substantially lacking the nucleic acids intervening the epitope-coding nucleic acids are also provided.

4 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 549 base pairs
        ( B ) TYPE: nucleic acid
        ( C ) STRANDEDNESS: double
        ( D ) TOPOLOGY: linear ( i i ) MOLECULE TYPE: Oligonucleotide ( i x ) FEATURE:
        ( A ) NAME/KEY: CDS
        ( B ) LOCATION: 10..538

( x i ) SEQUENCE DESCRIPTION: SEQ ID NO:1:

```
CCCGGATCC ATG ACT TCA GTA GAA AAT GCT CAA CAA GAT AAA GGA ATT          48
          Met Thr Ser Val Glu Asn Ala Gln Gln Asp Lys Gly Ile
           1               5                      10

GCA ATA CCA CAC GAC ATA GAT CTC GGA GAA TCT CGG GTT GTT ATT CAA        96
Ala Ile Pro His Asp Ile Asp Leu Gly Glu Ser Arg Val Val Ile Gln
    15              20                  25

GAT TAT GAT AAT CAA CAC GAA CAA GAT CGG CCT ACT CCA AGT CCT GCG       144
Asp Tyr Asp Asn Gln His Glu Gln Asp Arg Pro Thr Pro Ser Pro Ala
30                  35                  40                  45

CCG TCA CGT GGA GGC GGA AAT ACA ACA GCA TCA GAT CAA CTG CTG GTT       192
Pro Ser Arg Gly Gly Gly Asn Thr Thr Ala Ser Asp Gln Leu Leu Val
                50                  55                  60

GAA AAT GCA GCA GGA CAT CGA GTC GCA ATA GGA GGA GGA CGG CCT TTA       240
Glu Asn Ala Ala Gly His Arg Val Ala Ile Gly Gly Gly Arg Pro Leu
                65              70                  75

GGA CTT CAA GGA TGC GCA TTT CAA TCA ACA GTA GCA GAG CTT CAA CGT       288
Gly Leu Gln Gly Cys Ala Phe Gln Ser Thr Val Ala Glu Leu Gln Arg
            80                  85                  90

CTT AAA ATG AAA GTA GGA AAA ACT CGA GAA CTA GGA GGA GGA GCA AAC       336
Leu Lys Met Lys Val Gly Lys Thr Arg Glu Leu Gly Gly Gly Ala Asn
        95                  100                 105

CCA CCA GAT CAT TCA GCA CCA CTA GGC GTA ACA AGA CCA TCA GCT CCT       384
Pro Pro Asp His Ser Ala Pro Leu Gly Val Thr Arg Pro Ser Ala Pro
110             115                 120                 125

CCT CTA CCA CAT GTT GTT GAT CTT CCA CAA CTA GGA CCA CGG CGG GGA       432
Pro Leu Pro His Val Val Asp Leu Pro Gln Leu Gly Pro Arg Arg Gly
                130                 135                 140

GGA GGA GCA AAT CAA CCT GGA CAT CTG GCA CCT CTG GGA GAA ATA CGA       480
Gly Gly Ala Asn Gln Pro Gly His Leu Ala Pro Leu Gly Glu Ile Arg
            145                 150                 155

CCT TCA GCG CCA CCT CTG CCT CCT GTT GCA GAT CTG CCT CAA CCT GGA       528
Pro Ser Ala Pro Pro Leu Pro Pro Val Ala Asp Leu Pro Gln Pro Gly
        160                 165                 170

CTG CGG CGG T AAGAATTCGG G                                            549
Leu Arg Arg
175
```

( 2 ) INFORMATION FOR SEQ ID NO:2:

( i ) SEQUENCE CHARACTERISTICS:

( A ) LENGTH: 176 amino acids
        ( B ) TYPE: amino acid
        ( D ) TOPOLOGY: linear ( i i ) MOLECULE TYPE: polypeptide ( x i ) SEQUENCE DESCRIPTION: SEQ ID NO:2:

```
Met Thr Ser Val Glu Asn Ala Gln Gln Asp Lys Gly Ile Ala Ile Pro
 1               5                  10                  15
His Asp Ile Asp Leu Gly Glu Ser Arg Val Val Ile Gln Asp Tyr Asp
             20                  25                  30
Asn Gln His Glu Gln Asp Arg Pro Thr Pro Ser Pro Ala Pro Ser Arg
         35                  40                  45
Gly Gly Gly Asn Thr Thr Ala Ser Asp Gln Leu Leu Val Glu Asn Ala
     50                  55                  60
Ala Gly His Arg Val Ala Ile Gly Gly Gly Arg Pro Leu Gly Leu Gln
 65                  70                  75                  80
Gly Cys Ala Phe Gln Ser Thr Val Ala Glu Leu Gln Arg Leu Lys Met
                 85                  90                  95
Lys Val Gly Lys Thr Arg Glu Leu Gly Gly Ala Asn Pro Pro Asp
                100                 105                 110
His Ser Ala Pro Leu Gly Val Thr Arg Pro Ser Ala Pro Pro Leu Pro
            115                 120                 125
His Val Val Asp Leu Pro Gln Leu Gly Pro Arg Arg Gly Gly Gly Ala
    130                 135                 140
Asn Gln Pro Gly His Leu Ala Pro Leu Gly Glu Ile Arg Pro Ser Ala
145                 150                 155                 160
Pro Pro Leu Pro Pro Val Ala Asp Leu Pro Gln Pro Gly Leu Arg Arg
                165                 170                 175
```

( 2 ) INFORMATION FOR SEQ ID NO:3:

( i ) SEQUENCE CHARACTERISTICS:
            ( A ) LENGTH: 21 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:3:

```
Ala Asn Pro Pro Asp His Ser Ala Pro Leu Gly Val Thr Arg Pro Ser
 1               5                  10                  15
Ala Pro Pro Leu Ala
                20
```

( 2 ) INFORMATION FOR SEQ ID NO:4:

( i ) SEQUENCE CHARACTERISTICS:
            ( A ) LENGTH: 19 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:4:

```
Pro Ser Ala Pro Pro Leu Pro His Val Val Asp Leu Pro Gln Leu Gly
 1               5                  10                  15
Pro Arg Arg
```

( 2 ) INFORMATION FOR SEQ ID NO:5:

( i ) SEQUENCE CHARACTERISTICS:
   ( A ) LENGTH: 16 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:5:

Asp Lys Gly Ile Ala Ile Pro His Asp Ile Asp Leu Gly Glu Ser Arg
1               5                   10                  15

( 2 ) INFORMATION FOR SEQ ID NO:6:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:6:

Asp Tyr Asp Asn Gln His Glu Gln Asp Arg Pro Thr Pro Ser Pro Ala
1               5                   10                  15

Pro Ser Arg ( 2 ) INFORMATION FOR SEQ ID NO:7:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:7:

Arg Pro Leu Gly Leu Gln Gly Cys Ala Phe Gln Ser Thr Val Ala Glu
1               5                   10                  15

Leu Gln ( 2 ) INFORMATION FOR SEQ ID NO:8:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:8:

Gln Ser Thr Val Ala Glu Leu Gln Arg Leu Lys Met Lys Val Gly Lys
1               5                   10                  15

Thr Arg Glu Leu
            20

( 2 ) INFORMATION FOR SEQ ID NO:9:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:9:

Ala Asn Gln Pro Gly His Leu Ala Pro Leu Gly Glu Ile Arg Pro Ser
1               5                   10                  15

Ala Pro Pro Leu Ala
            20

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Pro Ser Ala Pro Pro Leu Pro Pro Val Ala Asp Leu Pro Gln Pro Gly
1               5                   10                  15

Leu Arg Arg ( 2 ) INFORMATION FOR SEQ ID NO:11:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Thr Ser Val Glu Asn Ala Gln Gln Asp Lys Gly Ile Ala Ile Pro His
1               5                   10                  15

Asp Ile Asp Leu
            20

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Asn Thr Thr Ala Ser Asp Gln Leu Leu Val Glu Asn Ala Ala Gly His
1               5                   10                  15

Arg Val Ala

MOSAIC POLYPEPTIDE AND METHODS FOR DETECTING THE HEPATITIS E VIRUS

This application is a continuation-in-part application of U.S. Ser. No. 07/965,667, filed Oct. 21, 1992.

BACKGROUND OF THE INVENTION

1. Field of the Invention

The invention pertains to methods and compositions for detecting anti-hepatitis E virus activity in a subject. The compositions include nucleic acids encoding mosaic polypeptides of hepatitis E virus and mosaic polypeptides of hepatitis E virus. The methods include serologic diagnosis of hepatitis E viral infection using the mosaic polypeptides of this invention.

2. Background Art

Hepatitis E virus (HEV) is a recently discovered agent of enterically transmitted non-A, non-B hepatitis (ET-NANB). The disease remains a serious problem in many developing countries. Unlike other agents of viral hepatitis, HEV infection is often associated with high mortality rates in infected pregnant women.

The first reported outbreak of ET-NANB hepatitis occurred in New Delhi, India in 1955. However, only after serologic tests for IgM anti-hepatitis A virus became available to exclude hepatitis A virus as the cause, was this very large outbreak recognized as ET-NANB hepatitis. Since that time epidemics of ET-NANB infection have been documented in many countries.

Until recently, the diagnosis of ET-NANB hepatitis outbreaks could only be based upon the absence of serologic markers of hepatitis A virus (HAV) and hepatitis B virus (HBV). Subsequently, specific tests for the detection of the ET-NANB hepatitis were based upon immune electron microscopy (IEM), in which a small volume of a stool suspension from acutely infected individuals is incubated with acute- or convalescent-phase sera and examined by electron microscopy (Bradley et al. *PNAS USA* 1987;84:6277–6281, 1987). IEM, thus identified 27–32 nm virus-like particles using acute and convalescent phase sera as the source of antibody. However, since most clinical specimens do not contain sufficient virus-like particles to visualize using IEM, this method is not useful for clinical or epidemiological analysis.

Three open reading frames (ORF) have been identified (Tam et al. *Virology,* 185:120–131, 1991). Two type-common HEV epitopes were identified at the C-terminus of proteins encoded by ORF2 and ORF3 (Reyes et al. *Gastroenterologia Japonica* 26 (suppl.3): 142–147, 1991b; Ichikawa et al. *Immunol.* 35:535–543, 1991). These epitopes were expressed as large hybrid proteins with beta-galactosidase or glutathione-S-transferase and were recognized in an enzyme immunoassay by antibodies from acute- and convalescent-phase sera obtained from experimentally infected cynomologus macaques (Reyes et al., in "Viral hepatitis C,D,E", T. Shikata, R. H. Purcell, T. Uchida (Eds.) Elsevier Science Publishers, NY, pp.237–245, 1991a) or humans (Goldsmith et al., *Lancet* 339:328–331, 1992). These hybrid proteins have the disadvantage that the chimeric part of protein can negatively influence folding, and thus, antibody recognition. Furthermore, individuals may have antibodies expressed to the chimeric sequences, resulting in false positive diagnoses.

Reyes et al (in "Viral hepatitis C,D,E", T Shikata, R. H. Purcell, T. Uchida (Eds.) Elsevier Science Publishers, NY, pp.237–245, 1991) demonstrated that a short fragment of the C-terminal region of the protein encoded by ORF3, obtained by expression of DNA derived from the HEV genome of the Burma strain did not react with sera from cynomologus macaques infected with the Mexico strain of HEV. Conversely, expressed recombinant protein derived from the Mexico strain did not react with sera from macaques infected with the Burma strain of HEV (Yarbough et al. *J. Virol.* 65:5790–5797, 1991). Sequence comparison of the two strains at the C-terminal region of ORF3 revealed a 78% homology (Yarbough et al., 1991). Thus, strain-specific immune responses of subjects can result in false negative diagnoses using the available technology.

A strategy for the construction of mosaic proteins retaining the antigenic reactivity of a natural prototype antigen has been recently applied to the hepatitis B surface antigen (HBsAg) (Kumar et al. *Gene* 110:137–144, 1992). This protein was composed of two antigenic epitopes from the preS-protein and a short region modeling the HBsAg conformational antigenic determinant "a". Antigenic properties of these epitopes can be successfully modeled with short synthetic peptides. The artificial HBV protein also retained the immunoreactivity of the introduced HBsAg antigenic epitopes.

Recently, an HCV antigen was constructed by joining 3 large segments of proteins (266, 363,and 119mers) into one polypeptide chain (Chien et al. *Proc. Nat'l Acad. Sci.* USA 89:10011–10015 (1992). There are also examples in the literature of successful expression of small antigenically active regions with carrier proteins. These antigens lack sensitivity.

None of the above-described HEV peptides or recombinant antigens provide a sensitive and specific means for diagnosing HEV infection. Thus, because of the lack of sensitivity and difficulty of performing the previously available tests, there exists a need for a rapid, simple and highly sensitive and specific diagnostic test for HEV infection.

The invention satisfies these needs with an artificial polypeptide containing a mosaic of antigenic epitopes from the ORF2 protein and from the ORF3 protein of the HEV Burmese and Mexican strains combined together. The "mosaic" protein is a valuable reagent for diagnostic tests for the detection of anti-HEV activity.

SUMMARY OF THE INVENTION

A nucleic acid encoding a mosaic hepatitis E virus (HEV) polypeptide consisting essentially of the amino acid sequence defined in the Sequence Listing as SEQ ID NO:2 is provided. The mosaic polypeptide encoded by the present nucleic acid is highly sensitive and specific for HEV antibodies produced in a subject in response to HEV infection. A nucleic acid encoding epitopes 5, 6, 22, 23, 28 and 29 of hepatitis E virus and substantially lacking the nucleic acids intervening the epitope-coding nucleic acids in the native hepatitis E virus is also provided.

An isolated nucleic acid that selectively hybridizes under stringent conditions with the mosaic polypeptide-encoding nucleic acid and has at least 70% sequence identity with SEQ ID NO:1 is provided. Also provided are such nucleic acids having at least 80%, 90% and 95% sequence identity.

A polypeptide encoded by the nucleic acid consisting of the nucleotide sequence defined in the Sequence Listing as SEQ ID NO:1 is provided. Polypeptides encoded by the present selectively hybridizing nucleic acids, and nucleic acids encoding the epitopes of peptides 5, 6, 23, 28 and 29 of HEV and substantially lacking the nucleic acids intervening the epitope-coding nucleic acids are also provided.

DETAILED DESCRIPTION OF THE INVENTION

Nucleic Acids

A nucleic acid encoding a mosaic hepatitis E virus (HEV) polypeptide consisting essentially of the amino acid sequence defined in the Sequence Listing as SEQ ID NO:2 is provided. The mosaic polypeptide encoded by the present nucleic acid is highly sensitive and specific for HEV antibodies produced in a subject in response to HEV infection. A specific example of the nucleic acid encoding a mosaic hepatitis E virus (HEV) polypeptide of the invention consists of the nucleotide sequence defined in the Sequence Listing as SEQ ID NO:1. However, it is clear that this mosaic polypeptide can be encoded by many nucleic acids, because of the degeneracy of the genetic code.

An isolated nucleic acid that selectively hybridizes under stringent conditions with the mosaic polypeptide-encoding nucleic acid and has at least 70% sequence identity with SEQ ID NO:1 is provided. Also provided are such nucleic acids having at least 80%, 90% and 95% sequence identity. Therefore, the selectively hybridizing nucleic acids when in double stranded form encode unique antigenic proteins which can be used to detect anti-HEV in a sample. Such nucleic acids by the nature of being selectively hybridizing would not hybridize with native HEV sequences under stringent conditions. "Isolated" means separated from some of the other naturally occurring nucleic acids of HEV.

"Stringent conditions" refers to the washing conditions used in a hybridization protocol. In general, the washing conditions should be as stringent as possible (i.e., a combination of temperature and salt concentration should be chosen so that the denaturation temperature is approximately 5°–20° C. below the calculated $T_m$ of the hybrid under study). The temperature and salt conditions can be determined empirically in preliminary experiments in which samples of reference DNA immobilized on filters are hybridized to the probe of interest and then washed under conditions of different stringencies.

A nucleic acid of the invention can include coding sequences for fewer than all of the epitopes encoded by the nucleic acid of SEQ ID NO:1. For example, a nucleic acid encoding the epitopes that correspond to peptides 5, 6, 22, 23, 28 and 29 of hepatitis E virus and substantially lacking the nucleic acids intervening the epitope-coding nucleic acids in the native hepatitis E virus is provided. The nucleic acid can also encode one or more of the epitopes that correspond to peptides 13, 33, 12, 40 in addition to those specified above. It is clear that such a nucleic acid can differ substantially in sequence from the exemplified nucleic acid and still encode an HEV mosaic protein of the present invention, because of the degeneracy of the genetic code.

More specifically, nucleic acids encoding the epitopes included in the following peptides can be used to generate a mosaic polypeptide of the invention: 5, 6, 22, 23, 28 and 29; 5, 6, 22, 23, 28, 29 and 13; 5, 6, 22, 23, 28, 29 and 33; 5, 6, 22, 23, 28, 29 and 12; 5, 6, 22, 23, 28, 29 and 40; 5, 6, 22, 23, 28, 29, 13 and 33; 5, 6, 22, 23, 28, 29, 13 and 12; 5, 6, 22, 23, 28, 29, 13 and 40; 5, 6, 22, 23, 28, 29, 13, 33 and 12; 5, 6, 22, 23, 28, 29, 13, 33, 12 and 40; 5, 6, 22, 23, 28, 29, 13, 12 and 40; 5, 6, 22, 23, 24, 28, 29, 13, 33 and 40. The peptides are shown in Tables 1 and 2. As can be seen in the tables, the some of the peptides include sequences that overlap the sequence of an adjacent peptide. When used together in a mosaic polypeptide the epitopes are generally contiguous, except for linking amino acids, and do not duplicate the overlapping sequences.

The arrangement of the epitope coding sequences can be as exemplified by SEQ ID NO:1. In those nucleic acids selective hybridization under stringent conditions can be obtained.

Alternatively, a mosaic polypeptide can be encoded by a nucleic acid having a different arrangement of HEV epitope coding nucleic acids. For example, in a mosaic polypeptide of the invention, the epitope(s) corresponding to peptides 22 and 23 can be positioned at the C-terminus of the protein. These epitopes are conformation dependent and thus will act as a better antigen when positioned in an order that more closely resembles the order in the native HEV ORF 2.

The nucleic acids can include sequences that encode amino acids that link the epitopic regions of the polypeptide. The purpose of these linking amino acids is to permit folding of the mosaic polypeptide in a manner that maximizes the modeling and exposure of the epitopes to antibodies present in samples being tested. The nucleic acids can encode glycine linkers (SEQ ID NO:1), linkers comprising both serine and glycine and other linking amino acids determined to permit proper folding and display of the epitopes. The size of the linking region can vary within the limits imposed by the modeling function of the mosaic polypeptide, generally ranging from 2 to 6 amino acids.

The feature of any of the above nucleic acids is that the nucleic acid encodes a mosaic polypeptide that can detect HEV antibodies in serum. The particular mosaic polypeptide encoded by the nucleic acid can be tested to determine its effectiveness, compared to previous HEV diagnostic assays or to the mosaic polypeptide exemplified by SEQ ID NO:2, by the assays taught in the Examples.

Mosaic Polypeptides

An HEV mosaic polypeptide consisting essentially of the amino acid sequence defined in the Sequence Listing as SEQ ID NO:1 is provided. A polypeptide encoded by the present selectively hybridizing nucleic acid is also provided. The polypeptide can contain a mosaic of three antigenically active dominant regions from the protein encoded by HEV open reading frame (ORF) 2, one antigenically active region from the protein encoded by ORF3 of the Burma HEV strain, and one antigenic region from the protein encoded by ORF3 of the Mexico HEV strain as further described in the Examples.

An example of the present HEV mosaic polypeptide (shown in SEQ ID NO:2) contains only short antigenically active regions that were shown to be necessary for the detection of anti-HEV activity in sera (Yarbough et al. *J. Virol.* 65:5790–5797, 1992; Favorov et al. *J. Virol. Meth.* (in press) 1993; Khudyakov et al. *Virol.* 194:89–96, 1993; Dawson et al. *J. Virol. Meth.* 38:175–186, 1992; Goldsmith et al. *Lancet* 229:328–331, 1992). The present mosaic polypeptide does not contain long inter-epitopic diagnostically irrelevant sequences. Rather, the polypeptide is composed of relatively independent small antigenic domains. Such a design allows for the generation of other HEV specific mosaic proteins by introduction of additional antigenic regions or several copies of the same antigenic region without significant affect on the overall structure and size of the protein.

An HEV mosaic polypeptide comprising peptides 5, 6, 22, 23, 28 and 29 of hepatitis E virus and substantially lacking the amino acids intervening the corresponding epitopes in the native hepatitis E virus is provided. The HEV mosaic polypeptide can also comprise one or more of peptides 13, 33, 12, 40 or there corresponding epitopes in addition to those specified above. The arrangement of the epitopes can be as exemplified by SEQ ID NO:2. Alternatively, the mosaic polypeptide can have a different arrangement of HEV epitopes. An important feature of any of the HEV mosaic polypeptides of the invention is that the mosaic polypeptide can detect HEV antibodies in serum or other body fluids or tissues.

Other HEV mosaic polypeptides are constructed as described herein, using the above described selectively hybridizing nucleic acids, which encode a subset of the epitopes disclosed in SEQ ID NO:2. Their effectiveness in the present diagnostic methods is confirmed as provided in the Examples. Other HEV mosaic polypeptides are constructed as described herein, using other HEV immunodominant epitopes provided by the invention.

The mosaic polypeptides can be synthesized as described below using nucleic acids in recombinant vectors and hosts or by direct synthesis using peptide synthesis methods. If direct synthesis is used, various linking molecules can be used to join the epitopic regions of the mosaic polypeptide, including amino acids or other kinds of linking molecules that do not appreciably negatively effect the specificity or sensitivity of the mosaic protein.

Vectors and Hosts

Both the mosaic polypeptide-encoding nucleic acid and the selectively hybridizing nucleic acids of the invention can be in a vector suitable for expression of the nucleic acid. The nucleic acid in a vector can be in a host suitable for expression of the nucleic acid. An example of the present HEV mosaic polypeptide, was expressed in *E. coli* as chimera with glutathione S-transferase (GST) or beta-galactosidase as further described in the Examples.

There are numerous *E. coli* expression vectors known to one of ordinary skill in the art useful for the expression of the antigen. Other microbial hosts suitable for use include bacilli, such as *Bacillus subtilus,* and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Diagnostic Methods

The invention also provides a method of detecting hepatitis E virus infection in a subject comprises the steps of (a) contacting an antibody-containing sample from the subject with an amount of the mosaic polypeptide encoded by the nucleic acid of SEQ ID NO:1, and (b) detecting an antibody recognition reaction of the polypeptide and an antibody in the sample, a reaction indicating the existence of hepatitis E virus infection.

Another method of detecting hepatitis E virus infection in a subject comprises the steps of (a) contacting an antibody-containing sample from the subject with an amount of the polypeptide encoded by the selectively hybridizing nucleic acid of the invention, and (b) detecting an antibody recognition reaction of the polypeptide and an antibody in the sample, a reaction indicating the existence of hepatitis E virus infection.

In the diagnostic methods taught herein, the amount of mosaic polypeptide will be that amount which will result in a detectable antibody recognition reaction if HEV antibodies are present. The mosaic polypeptide can be bound to a substrate and contacted by a fluid sample such as blood, serum, urine or saliva. This sample can be taken directly from the patient or in a partially purified form. In this manner, antibodies specific for HEV (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, nonspecifically with the or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change).

HEV mosaic polypeptides of the invention (GST and beta-galactosidase chimeras, described in the Examples) were analyzed using a panel of human anti-HEV positive and negative sera as further described in the Examples. The data obtained demonstrate the utility of the present mosaic proteins in methods for diagnosing HEV infection.

Vaccines

The mosaic polypeptides of this invention can be used in the construction of a vaccine comprising an immunogenic amount of the mosaic polypeptide and a pharmaceutically acceptable carrier. The vaccine can also be potentially cross-reactive with antibodies to other antigens, for example, in a multivalent vaccine. The vaccine can then be used in a method of preventing HEV infection.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

TABLE 1

PRIMARY AND PREDICTED SECONDARY STRUCTURE FOR SELECTED REGIONS OF THE PROTEIN ENCODED BY ORF2 OF HEV GENOME

| Peptide | Position | Primary and secondary structure | |
|---|---|---|---|
| 33 | 414–433 | TSVENAQQDKGIAIPHDIDL<br>sssttttssssssstttss | (SEQ ID NO: 11) |
| 12 | 422–437 | DKGIAIPHDIDLGESR<br>cttsssttccttttc | (SEQ ID NO: 5) |
| 13 | 442–460 | DYDNQHEQDRPTPSPAPSR<br>ccccccccccccccccttc | (SEQ ID NO: 6) |
| 40 | 562–580 | NTTASDQLLVENAAGHRVA<br>sstttcsssstttccss | (SEQ ID NO: 12) |
| 22 | 631–648 | RPLGLQGCAFQSTVAELQ<br>ctttccccccccchhhhh | (SEQ ID NO: 7) |
| 23 | 641–660 | QSTVAELQRLKMKVGKTREL<br>ccchhhhhhccccccccc | (SEQ ID NO: 8) |

Elements of secondary structure are indicated as follow: h - alpha-helix; s - beta-sheet; t - beta-turn; c - random coil

TABLE 2

PRIMARY AND PREDICTED SECONDARY STRUCTURE FOR THE SELECTED REGIONS OF THE PROTEIN ENCODED BY ORF3 OF HEV GENOME

| Peptide | Position | Primary and secondary structure | |
|---|---|---|---|
| 5 | 91–110 | ANPPDHSAPLGVTRPSAPPLA<br>ccttcccctttcccttcccc | (SEQ ID NO: 3) |
| 6 | 105–123 | PSAPPLPHVVDLPQLGPRR<br>ttccccccccctttcccc | (SEQ ID NO: 4) |
| 28 | 91–110 | ANQPGHLAPLGEIRPSAPPLA<br>ccttcccctttcccttcccc | (SEQ ID NO: 9) |
| 29 | 105–123 | PSAPPLPPVADLPQPGLRR<br>ttcccccccccttcccc | (SEQ ID NO: 10) |

Elements of secondary structure are indicated as follow: h - alpha-helix; s - beta-sheet; t - beta-turn; c - random coil
Peptides 28 and 29 represent the protein encoded by ORF3 of Mexico strain HEV (Yarbough et al., 1991).

The following examples are intended to illustrate, but not limit, the invention. While the protocols described are typical of those that might be used, other procedures known to those skilled in the art may be alternatively employed.

EXAMPLES

Synthetic oligodeoxynucleotides.

Oligodeoxynucleotides were synthesized with an automatic synthesizer (Applied Biosystem Model 480A) and purified by electrophoresis in 10% PAGE containing 7M urea in TBE buffer (0.045M Tris-borate, 0.001M EDTA, pH 8.3). Oligodeoxynucleotides were recovered from the gel by electroelution using the model 230A HPEC system (Applied Biosystem, Foster City, Calif.) according to the manufacturer's protocol.

Synthetic gene assembly.

The synthetic gene encoding this mosaic protein was assembled from 3 subfragments. Two of these subfragments were synthesized by PCR from 4 oligodeoxynucleotides each. Oligonucleotides were used at a final concentration of between 10 and 100 pmol in each reaction. The third subfragment was synthesized using only 2 oligonucleotides at a concentration of 100 pmol per reaction. All subfragments were synthesized by adding the appropriate oligonucleotides to the reaction mixture, followed by 30 cycles of PCR as follows: 94° C. for 45 sec, 65° C. for 20 sec, and 72° C. for 1 min. The synthesized subfragments were treated with the appropriate restriction endonucleases with the recognition sites located at the termini of each fragment, and then ligated in 10μl of a solution containing all three subfragments, 50 mM Tris-HCl, pH 7.5, 10mM $MgCl_2$, 1 mM DTT, 1 mM ATP, and 10 units of DNA ligase (Pharmacia, Piscataway, N.J.) for 6 h. One μl of the ligase reaction mixture was used to amplify the fragment by PCR to provide the full-length DNA using PCR conditions described above and using the two terminal oligonucleotides as primers. Amplified full-length DNA was recovered from agarose gel by a DEAE procedure and treated with restriction endonucleases to confirm the structure of the synthesized gene.

All regions of the ORF2 and ORF3 proteins containing immunoreactive epitopes in both the Burmese and Mexican strains of HEV were included in the artificial mosaic protein. Each antigenic region was separated from each other by 3 consecutive glycine residues (SEQ ID NO:1).

Plasmid construction.

To obtain restriction endonuclease recognition sites suitable for insertion of the synthetic fragment into plasmids, the fragment was reamplified by PCR using a pair of primers with specially designed restriction sites. PCR was carried out as described above. For cloning the fragment with the vector pGEX-2T (Pharmacia Biotech Inc., Piscataway, N.J.), the synthetic DNA was provided with BamHI- and EcoRI-sites. For cloning of the fragment with the vector pAX-4a+ (United States Biochemical Co., Cleveland, Ohio), the DNA fragment was provided with EcoRI- and SalI-sites.

The initial plasmid obtained by the insertion of the synthetic DNA fragment into pGEX-2T was designated pMEG330. pMEG330 contains the gene encoding for a fusion protein with the N-terminal part represented by glutathione S-transferase (GST) and the C-terminal half represented by the artificial mosaic protein.

To analyze the fidelity of the assembled gene, the primary structure of the cloned synthetic DNA fragments was determined using an additional set of oligodeoxynucleotides as primers. Unexpectedly, a deletion within the synthetic gene was found which resulted in the elimination of a glycine spacer and a part of the HEV Burma-specific ORF3 antigenic epitope. The deletion did not change the phase of translation, but resulted in the expression of a protein 13 aa shorter. To correct the structure of the synthetic gene, the DNA fragment located between the XhoI- and Sau 96A-sites was reassembled and after sequence confirmation, the deletion containing region of the plasmid pMEG330 was replaced with the corrected DNA fragment. The resulting plasmid, pMEG330–45, contains the synthetic gene encoding for the artificial mosaic protein of the originally designed structure.

Additionally, the corrected synthetic gene was inserted into the vector p4a-2X, resulting in the plasmid pMEL301. This plasmid encodes for a fusion protein with the N-terminal part represented by the beta-galactosidase and the C-terminal part represented by the HEV mosaic protein. For each plasmid, the sequence of the cloned synthetic mosaic gene was verified by the polymerase chain terminator method.

Mosaic polypeptide expression and purification.

To express the fusion proteins, *E. coli* JM109 competent cells (Invitrogen, Co., San Diego, Calif.) were transformed with the plasmids pMEG330–45 and pMEL301. Cells were grown in LB medium containing 100 μg/ml of ampicillin until an optical density at 600 nm was equal to 0.6 after which the promoter controlling the expression of the fusion proteins was activated by the addition of isopropyl-beta-D-thiogalacto- pyranoside (IPTG) at a final concentration of 1 mM. After 4–6 hours of growth at 37° C., the cells were harvested and a lysate was prepared.

The glutathione S-transferase-HEV mosaic fusion protein (GST-HE) encoded by the pMEG330–45 was purified by affinity chromatography (Smith, D. B. and Johnson, K. S., *Gene* 67:37–40, 1988) using a glutathione-Sepharose 4B column (Pharmacia LKB Biotechnology, Piscataway, N.J.).

Synthetic peptides.

Peptides were synthesized by FMOC-chemistry (Barany and Merrifield, 1980) on an ACT Model MPS 350 multiple peptide synthesizer (Advanced Chemtech, Louisville, Ky.) according to the manufacturer's protocols. After characterization by amino acid analysis, high performance liquid chromatography, and capillary electrophoresis, peptides were directly used for conjugation to bovine serum albumin (BSA) or keyhole limpet hemocyanin (KLH) using a commercially available conjugation kit (Pierce, Rockford, Ill.). The synthetic peptides were used to immunize guinea pigs to obtain anti-peptide sera for use in subsequent tests.

Guinea pig anti-synthetic peptide sera.

Conjugated synthetic peptides were mixed with CYTREX Titer-Max adjuvant and injected subcutaneously into guinea pigs at 4 sites. Each site was injected with approximately 50 μl of the mixture containing 8–18 μg of conjugated peptides. After 2 weeks the animals were boosted. These animals were bled 4 weeks later.

Human sera.

Sera from HEV outbreaks in Mexico in 1987 (n=5), Somalia in 1988 (n=10), Tadjikistan in 1990 (n=11), and Kenya in 1991 (n=23) were randomly selected from collections deposited in the Hepatitis Branch, National Center for Infectious Diseases, Centers for Disease Control and Prevention, Atlanta, Ga. and the D. I. Ivanovsky Institute of Virology, Moscow, Russia. Serum specimens obtained from normal blood donors, from persons infected with hepatitis A, hepatitis B and hepatitis C viruses were collected from HEV nonendemic regions of the world and used as negative controls.

Proper modeling of the antigenic epitopes in the mosaic protein.

*E. coli* cells transformed with the plasmids pMEG330–45 and pMEL301 produce polypeptides of the expected molecular weight of approximately 45 KDa and 125 KDa, respectively. To verify the presence of each HEV-specific antigenic region included in the mosaic protein, these proteins were analyzed by Western Blot assay and enzyme immunoassay with sera obtained by immunization of guinea pigs with the corresponding synthetic peptides.

Western Blot assay.

Aliquots of the lysate were analyzed by Western blot (Harlow, E., Lane, D. (1988) Antibodies. A laboratory manual. Cold Spring Harbor, N.Y., pp. 471–510). Nitrocellulose filters containing immobilized proteins were incubated at 20° C. for 2 h with guinea pig anti-synthetic peptide sera or human sera diluted 100 times in 50 mM Tris-HCl, pH 7.5, containing 0.5% Triton X-100, 1% gelatin, and 1% bovine serum albumin (NET). The filters were washed with NET three times, and then incubated for 1 h with affinity chromatography purified anti-human IgG or anti-guinea pig IgG coupled to horseradish peroxidase (Boehringer Mannheim, Germany) diluted 1:5000 in NET. After washing, diaminobenzidine (Sigma, St. Lous, Mo.) and hydrogen peroxide were used to develop the reaction.

For identification of the HEV ORF2 antigenic region at aa position 394–470, sera obtained to the peptide 33 comprising the sequence at aa position 414–433 (Khudyakov et al. *Virol.* 198:390–393, 1994) and to the peptide 13 comprising the sequence at aa position 442–460 (Khudyakov et al. 1993) were used. The immunoreactivity of the ORF2 antigenic region at aa position 562–580 was confirmed with guinea-pig anti-peptide 40 serum (Khudyakov et al., 1994). The ORF2 region at aa position 631–660 was identified with guinea-pig sera to peptide 23 (641–660aa) (Khudyakov et al.1993). The ORF3 antigenic regions were detected using anti-peptide 5 (91–110 aa) and anti-peptide 6 (105–123 aa) sera for the Burmese strain and anti-peptide 28 (91–110 aa) and anti-peptide 29 (105–123 aa) sera for the Mexican strain (Khudyakov et al. 1993). The results of the Western Blot assay clearly indicate the presence and immunoreactivity of all HEV-specific antigenic regions designed in the mosaic protein.

A confirmatory Western blot assay was carried out according to Favorov et al. (1992). Purified insoluble trpE fusion proteins C2 and C2-1 containing different fragments of the HEV protein encoded by ORF2 (Purdy et al., 1992) were kindly provided by Dr. M. Purdy, Hepatitis Branch, Centers for Disease Control and Prevention, Atlanta, Ga.

EIA for anti-HEV.

To further confirm the accessibility of each antigenic region included in the artificial HEV-specific mosaic protein to epitope specific antibodies, the GST-fusion protein encoded by the plasmid pMEG330–45 was affinity purified (see Materials and Methods) and passively adsorbed on the surface of the microtiter wells. Guinea-pig anti-peptide sera which were used in the Western Blot assay were also utilized in the EIA format. For comparison, the corresponding synthetic peptides and peptide conjugates were also used in EIA.

Affinity purified GST-HE protein (110 μl) at a concentration of 5 μg/ml was adsorbed to microtiter wells (Immulon II, Dynatech Laboratories, Inc.). Human and guinea pig sera were diluted 1:100 in 0.1M phosphate-buffered saline, pH7.5, containing 0.1% Tween 20 and 10% normal goat serum. Binding of antibodies to the recombinant protein adsorbed to the surface of the wells of microtiter plates was identified with affinity purified antibodies to human or guinea pig IgG coupled to horseradish peroxidase (Company). The cutoff, expressed as a P/N ratio, was statistically established as a mean of negative controls plus 3 standard deviations (SD) above the mean, and was equal 2.1, where P represents the optical density value at 490 nm of the anti-HEV positive specimen and N represents the optical density value of negative controls. Typically, the optical density value for negative controls was 0.05±0.001.

All anti-peptide sera immunoreacted with the mosaic protein. This observation demonstrates the accessibility of all HEV-specific antigenic regions included in the artificial protein to the anti-synthetic peptide antibodies. The degree of immunoreactivity was variable depending on the epitope and anti-peptide serum. For example, the epitope from the C-terminal region of the HEV ORF2 protein demonstrated a lower antigenic reactivity with the corresponding anti-peptide serum compared to other antigenic regions. On the other hand, anti-peptide sera obtained to the synthetic peptides 28 and 29 (Table 1) were more immunoreactive with the region of the mosaic polypeptide derived from the C-terminal part of the ORF3 protein of the Mexican strain than with the corresponding synthetic peptides. This observation may be due to a different immunologic reactivity of anti-peptide antibodies or to a different degree of antigenic epitope modeling in the mosaic protein compared to the natural antigens or synthetic peptides. The C-terminal antigenic epitopes of the Mexican HEV ORF3 protein are located at the C-terminus of the artificial mosaic protein, which mimics the manner these epitopes are represented in the natural antigen; whereas, the C-terminal region of the HEV ORF2 protein is positioned non-terminally within the artificial mosaic protein, in contrast to the manner these epitope are found in the natural antigen. The difference in the localization of these epitopes in the natural antigen and in the mosaic protein may affect their immunoreactive properties. Nonetheless, the antigenic reactivity of different HEV-specific antigenic epitopes as observed in our experiments demonstrate that the epitopes included in the mosaic protein are modeled in an immunoreactive manner.

An EIA using synthetic peptides or peptides conjugated to BSA was carried out essentially as described above with the exception that plates were coated with 5 µg of peptides or 0.5 µg of peptide conjugates per well as described elsewhere (Khudyakov et al., 1993; Favorov et al., 1994). Typically, the optical density value for negative controls was 0.02±0.002.

Diagnostic relevance of the mosaic polypeptide.

To ascertain the diagnostic potential of the mosaic protein, we used a panel of human sera obtained from HEV outbreaks in different regions of the world. A panel of 30 serum specimens obtained from normal blood donors, and from persons serologically positive for antibodies to hepatitis A, hepatitis B, and hepatitis C viruses from non-endemic regions of the world was used as negative controls. The anti-HEV status of all specimens was preliminarily determined by Western blot assay (Faroroy et al. 1992) and the recently developed synthetic peptide-EIA (Favorov et al 1993). All 30 serum specimens obtained from HEV outbreaks were found to contain HEV-specific IgG antibody. These sera also demonstrated strong IgG immune reactivity with the GST-mosaic protein. The range of P/N ratios for anti-HEV positive sera immunoreactive with the mosaic protein was 2.1–500. Statistical analysis was performed as stated above for the anti-HEV EIA. Some anti-HEV positive specimens had titers exceeding 1:50 000.

The protein encoded by plasmid PMEG330 containing a deletion of part of the HEV-specific sequence was also analyzed. It is noted that the deletion derivative mosaic protein demonstrated noticeably weaker antigenic reactivity compared to the full length protein. The antigenic reactivity of the deletion containing protein was somewhat improved by heat denaturation of the purified protein for 2 min at 85°–95° C. Surprisingly, heat denaturation degraded the antigenic properties of the protein containing the correct sequence. This variance in the antigenic properties of these two proteins may reflect a difference in modeling the macrostructure of those HEV-specific epitopes which are not directly affected by the deletion.

These results show that the combining of many different epitopic regions in one polypeptide chain cannot necessarily be expected to result in a properly folded mosaic antigen. For example, the HEV mosaic protein containing a small deletion of only few amino acids within the ORF3 antigenic region of the Burmese HEV strain dramatically diminished the antigenic property of the entire antigen. This result suggests that proper modeling of antigenic epitopes within mosaic proteins may require attention to the secondary and tertiary structure and may require the routine construction and testing of several variants of artificial antigens to determine their relative effectiveness.

Exclusion of crossreactive epitopes

It is known that 3–4% of antibodies specific to an infectious agent may also recognize some host-specific proteins. There are many examples of such crossreactivity of antibodies and this phenomenon may be, in part, responsible for false-positive results. In our experiments using synthetic peptides, we have previously identified a region at aa position 515–530 of the protein encoded by ORF2 (Khudyakov et al. 1994), that immunoreacted with approximately 10% of sera obtained from HEV non-endemic regions and shown to be devoid of anti-HEV activity by both Western Blot assay and synthetic peptide-EIA. This data suggests that this region may contribute to non-specific reactivity of the ORF2 protein. Exclusion of these regions from proteins used as immunodiagnostic reagents improved the specificity of these reagents and resulted in a more specific diagnostic test.

Accommodation of strain dependent immunoreactivity.

The HEV mosaic polypeptide connects, in one polypeptide chain, antigenic epitopes from the two different HEV proteins belonging to the two known HEV strains. For HEV, a strong strain dependent immunoreactivity of the ORF3 protein has been also observed in experiments using HEV infected cynomologous macaques (Yarbough et al. 1991). Although this strict strain specificity was not confirmed with human sera (Khudyakov et al. 1993), we have observed some affect of the primary structure of synthetic peptides derived from the C-terminal region of the ORF3 protein on the antigenic reactivity of these peptides with serum specimens from different parts of the world (Khudyakov et al. 1993). In support of this observation, data were obtained demonstrating the presence of strictly Burmese or Mexican strain-specific epitopes within the ORF3 protein (Khudyakov et al. J. Gen. Virol. 75, 1994). Additionally, it was shown that a combination of peptides derived from both HEV strains detected a greater percentage of anti-HEV positive sera than each of these peptides alone (Khudyakov et al. 1993).

Collectively, these data suggest that the antigens from the two HEV strains must be used for the development of tests for the detection of anti-HEV activity in sera. However, the application of only these epitopes was not sufficient for the detection of all cases of HEV infection (Khudyakov et al. 1993) and additional antigenic epitopes from the ORF2 protein should be used to improve the overall sensitivity (Favorov et al. 1993).

Throughout this application various publications are cited. The disclosures of these publications in their entireties are hereby incorporated by reference into this application in order to more fully describe the state of the art to which this invention pertains.

---

What is claimed is:

1. A mosaic polypeptide consisting of the amino acid sequence defined in the Sequence Listing as SEQ ID NO:2.

2. A method of detecting hepatitis E virus infection in a subject comprising:
    a. contacting an antibody-containing sample from the subject with an amount of the polypeptide of claim 1; and
    b. detecting an antibody recognition reaction of the polypeptide and an antibody in said sample, a reaction indicating the existence of hepatitis E virus infection.

3. A mosaic polypeptide which specifically binds hepatitis E virus-specific antibodies, comprising peptides 5, 6, 22, 23, 28 and 29 of hepatitis E virus, linked together by two to six amino acids or other linking molecules.

4. A method of detecting hepatitis E virus infection in a subject comprising:
    a. contacting an antibody-containing sample from the subject with an amount of the polypeptide of claim 3; and
    b. detecting an antibody recognition reaction of the polypeptide and an antibody in said sample, a reaction indicating the existence of hepatitis E virus infection.

\* \* \* \* \*